United States Patent
Yim et al.

(10) Patent No.: US 9,968,576 B2
(45) Date of Patent: *May 15, 2018

(54) COMPOSITION FOR PREVENTING OR TREATING NEURODEGENERATIVE DISEASES, CONTAINING RAMALIN

(71) Applicant: KOREA INSTITUTE OF OCEAN SCIENCE AND TECHNOLOGY, Gyeonggi-do (KR)

(72) Inventors: Joung Han Yim, Gyeonggi-do (KR); Il-Chan Kim, Gyeonggi-do (KR); Se Jong Han, Gyeonggi-do (KR); Dong-Gyu Jo, Gyeonggi-do (KR)

(73) Assignee: KOREA INSTITUTE OF OCEAN SCIENCE AND TECHNOLOGY, Gyeonggi-Do (KR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/520,100

(22) PCT Filed: Oct. 24, 2014

(86) PCT No.: PCT/KR2014/010057
§ 371 (c)(1),
(2) Date: Apr. 19, 2017

(87) PCT Pub. No.: WO2016/064009
PCT Pub. Date: Apr. 28, 2016

(65) Prior Publication Data
US 2017/0304244 A1 Oct. 26, 2017

(51) Int. Cl.
A61K 31/198 (2006.01)
A61K 45/06 (2006.01)
A61K 31/45 (2006.01)

(52) U.S. Cl.
CPC .................. *A61K 31/198* (2013.01)

(58) Field of Classification Search
CPC ....... A61K 31/198; A61K 45/06; A61K 31/45
See application file for complete search history.

(56) References Cited

U.S. PATENT DOCUMENTS

2014/0235719 A1* 8/2014 Yim .................. A61K 31/45
514/563

FOREIGN PATENT DOCUMENTS

| JP | H10-338678 A | 12/1998 |
|---|---|---|
| JP | 2005-509651 A | 4/2005 |
| JP | 2013-534517 A | 9/2013 |
| JP | 20103-534517 A | 9/2013 |
| KR | 10-1025612 B1 | 3/2011 |
| KR | 10-1182334 B1 | 9/2012 |
| KR | 10-1290745 B1 | 7/2013 |
| KR | 10-1326256 B1 | 11/2013 |

OTHER PUBLICATIONS

WebMD—http://www.webmd.com/alzheimers/tc/alzheimers-disease-prevention, Sep. 2010, 2 pages.*
Berg Aug. 29, 2010 1 page.*
Uttara et al. Curr Neuropharmacol 2009; 7(1):65-74.*
Cole et al. (Neurobiol Aging May.-Jun. 2000; 21(3):383-421.*
Block, M.L., et al., "Microglia-mediated neurotoxicity: uncovering the molecular mechanisms", "Nature Reviews, Neuroscience", Jan. 2007, pp. 57-69, vol. 8.
Boyden, E.D. et al., "Nalp1b controls mouse macrophage susceptibility to anthrax lethal toxin", "Nature Genetics", Feb. 2006, pp. 240-244, vol. 38, No. 2.
Chang, Y.-H., et al, "Inhibition of Melanogenesis by Ramalin from the Antarctic Lichen *Ramalina terebrata*", "Journal of the Society of Cosmetic Scientists of Korea", 2012, pp. 247-254, vol. 38, No. 3.
Donev, R., et al., "Neuronal death in Alzheimers disease and therapeutic opportunities", "Journal of Cellular and Molecular Medicine", 2009, pp. 4329-4348, vol. 13, No. 11-12.
Gelderblom, M., et al, "Temporal and Spatial Dynamics of Cerebral Immune Cell Accumulation in Stroke", "Stroke", May 2009, pp. 1849-1857, vol. 40, No. 5.
Goldmann, T., et al., "Love and death: microglia, NLRP3 and the Alzheimers brain", "Cell Research", May 2013, pp. 595-596, vol. 23, No. 5.
Halle, A., et al., "The NALP3 inflammasome is involved in the innate immune response to amyloid-b", "Nature Immunology", Aug. 2008, pp. 857-865, vol. 9, No. 8.
Heneka, M.T., et al., "NLRP3 is activated in Alzheimers disease and contributes to pathology in APP/PS1 mice", "Nature", Jan. 31, 2013, pp. 674-678, vol. 493.
Iadecola, C., et al., "Stroke research at a crossroad: Asking the brain for directions", "Nature Neuroscience", Nov. 2011, pp. 1363-1368, vol. 14, No. 11.
Laferla, F.M., "Pathways linking Ab and tau pathologies", "Biochemical Society Transactions", 2010, pp. 993-995, vol. 38, No. 4.
Lamkanfi, M., et al., "Inflammasomes and Their Roles in Health and Disease", "Annual Review of Cell and Developmental Biology", Sep. 10, 2012, pp. 137-161, vol. 28.
Lucin, K.M., et al., "Immune Activation in Brain Aging and Neurodegeneration: Too Much or Too Little?", "Neuron", Oct. 15, 2009, pp. 110-122, vol. 64.

(Continued)

*Primary Examiner* — Shirley V Gembeh
(74) *Attorney, Agent, or Firm* — Hultquist, PLLC; Steven J. Hultquist

(57) ABSTRACT

The present invention relates to a neurodegenerative disease treatment use, which is a novel use of Ramalin, and, more specifically, to a composition for preventing or treating neurodegenerative diseases, containing Ramalin, which has an inflammasome and BACE1 expression inhibitory activity. Ramalin according to the present invention has an effect of improving a cognitive ability by inhibiting the expression of an inflammatory factor, which contains an NLRP inflammasome protein, and BACE1, and is thus useful for preventing or treating memory disorder and neurodegenerative diseases.

4 Claims, 10 Drawing Sheets

(9 of 10 Drawing Sheet(s) Filed in Color)

(56) References Cited

OTHER PUBLICATIONS

Martinon, F., et al., "The Inflammasome: A Molecular Platform Triggering Activation of Inflammatory Caspases and Processing of proIL-b", "Molecular Cell", Aug. 2002, pp. 417-426, vol. 10.

Martinon, F., et al., "The Inflammasomes: Guardians of the Body", "Annual Review of Immunology", Dec. 8, 2008, pp. 229-265, vol. 27.

McGeer, P.L., et al., "Reactive microglia in patience with senile dementia of the Alzheimer type are positive for the histocompatibility glycoprotein HLA-DR", "Neuroscience Letters", Apr. 1, 1987, pp. 195-200, vol. 79.

Paudel, B., et al., "Antibacterial Activities of Ramalin, Usnic Acid and its Three Derivatives Isolated from the Antarctic Lichen *Ramalina terebrata*", "Zeischrift fur Naturfoschung. C, A journal of biosciences", Jan.-Feb. 2010, pp. 34-38, vol. 65, No. 1-2.

Paudel, B., et al., "Ramalin, a novel nontoxic antioxidant compound from the Antarctic lichen *Ramalina terebrata*", "Phytomedicine", Jul. 29, 2011, pp. 1285-1290, vol. 18.

Querfurth, H.W., et al., "Alzheimers Disease", "The New England Journal of Medicine", Jan. 28, 2010, pp. 329-344, vol. 362.

Note: For the non-patent literature citations that no month of publication is indicated, the year of publication is more than 1 year prior to the effective filing date of the present application.

Toda, N., et al, "Alzheimer's Disease, Cerebral Blood Flow, and Nitric Oxide", "Folia Pharmacol. Jpn.", 2010, pp. 20-24, vol. 135.

Toda, N., et al, "Alzheimer's Disease, Cerebral Blood Flow, and Nitric Oxide", "Folia Pharmacol. Jpn.", 2010, pp. 20-24, vol. 135 (English Abstract).

J-Stage, "www.jstage.jst.go.jp/article/toxp/33/0/33_0_19/_article", "J-Stage", 2006.

"J-Stage", 2006, Page(s) Machine Translation.

\* cited by examiner

COMPOSITION FOR PREVENTING OR TREATING NEURODEGENERATIVE DISEASES, CONTAINING RAMALIN

CROSS-REFERENCE TO RELATED APPLICATION

This application is a U.S. national phase under the provisions of 35 U.S.C. § 371 of International Patent Application No. PCT/KR2014/010057 filed Oct. 24, 2014. The disclosure of such international patent application is hereby incorporated herein by reference in its entirety, for all purposes.

TECHNICAL FIELD

The present disclosure relates to an use of treating a neurodegenerative disease, as a novel use of Ramalin, and more specifically, to a composition for preventing or treating neurodegenerative diseases, comprising Ramalin, which has an activity of inhibiting the expression of inflammasome and BACE1.

BACKGROUND ART

Alzheimer's disease (AD) is the most common neurodegenerative disease that causes dementia and has neuronal loss and cognitive disorder as progressive neurodegenerative disease symptoms (Donev et al., *J Cell Mol Med,* 13:4329-48, 2009). The AD has neuropathological features of extracellular amyloid-β (Aβ) plaques and intracellular nerve fiber tangles (Querfurth et al., *N Engl J Med.* 362(4): 329-44; LaFerla et al., *Biochem Soc Trans.* 38(4):993-5). The amyloid-β is generated by continuous division of an amyloid-β precursor protein (APP), which is mediated by beta-secretase 1 (BACE1) and presenilin/γ-secretase. Generation and aggregation of the amyloid-β play an important role to trigger a complex pathologic induction that causes neurodegeneration, entanglement of nerve fibers, inflammation and loss of neurons.

Activation of microneuroglial cells expressing neuroinflammation is another pathologic characteristic in the brain of a patient with the AD (McGeer et al., *Neurosci Lett,* 79:195-200, 1987). Further, the microneuroglial cells serve as latent pathogenic origins in many central nervous system (CNS) diseases including chronic neurodegenerative diseases such as AD, Parkinson's disease (PD), human immunodeficiency virus (HIV) dementia, and multiple sclerosis (Block et al., *Nat Rev Neurosci,* 8:57-69, 2007). The activated microneuroglial cells and leukocytes produce various inflammation mediators including anaphylatoxin complement, cytokine, chemokine, and prostaglandin (Gelderblom et al., *Stroke* 40(5):1849-57, 2009; Iadecola et al., *Nature Neuroscience* 14(11):1363-1368, 2011).

Studies on an inflammasome complex in peripheral tissues relate to production, secretion, and apoptotic and pyroptotic cell death of inflammatory cytokines (Lamkanfi et al., *Annu Rev Cell Dev Biol.* 28:137-61). NACHT, LRR and PYD domains-containing protein 1 (NLRP1) and NACHT, LRR and PYD domains-containing protein 3 (NLRP3) inflammasomes are cytoplasmic polymer complexes consisting of a NLRP1/3 receptor, apoptosis-associated speck-like protein containing a caspase recruitment domain (ASC), procaspase-1, procaspase-11 (homology with human procaspase-4 or 5), and X-linked inhibitor of apoptosis (XIAP) (Boyden et al., *Nat Genet* 38(2):240-4, 2006; Martinon et al., *Mol Cell* 10(2):417-26, 2002). The procaspase-1 is automatically activated by activation and homo-oligomerization of NLRP1 and NLRP3 receptors to be converted into the cleaved caspase-1 and form NLRP1 and NLRP3 inflammasomes (Lamkanfi et al., *Annu Rev Cell Dev Biol.* 28:137-61; Martinon et al., *Mol Cell* 10(2):417-26, 2002). Chronic accumulation of Aβ promotes activation of the microneuroglial cells in the AD (Goldmann et al., *Cell Res.* 23:595-6). An increase in IL-1β level is associated with the accumulation of Aβ (Lucin et al., *Neuron,* 64:110-22, 2009), and IL-1β is produced in an inactive pro-form for activation and secretion of caspase-1, and the activity of caspase-1 is regulated by the inflammasome. The NLRP3 inflammasome detects inflammatory crystal and aggregated proteins such as Aβ and is associated with chronic inflammatory diseases (Halle et al., *Nat Immunol* 9(8)857-65, 2008; Martinon et al., *Annu Rev Immunol* 27:229-65, 2009; Heneka et al., *Nature* 493(7434):674-8). An inflammatory substance induced by the activation of the NLRP inflammasome serves to mediate synaptic dysfunction, cognitive disorder, functional restriction of microneuroglial cells, and the like. The progression of the AD may be efficiently hindered by treatment of inhibiting activation of the NLRP inflammasomes and inflammasome-derived cytokines that play an important role in an Aβ-mediated inflammatory response.

Ramalin has an anti-oxidation effect at a concentration that cytotoxicity is almost not shown in human keratinocytes and fibroblasts (Paudel et al., *Phytomedicine.* 18(14):1285-90) and is known as an antioxidant that inhibits an inflammatory response.

The present inventors isolate Ramalin which is a novel compound from Ramalina terebrata which is a lichen that grows wild in King George Island, Antarctica in previous studies (Korea Patent No. 10-1025612), and provide a synthesis method of Ramalin (Korea Patent No. 10-1182334). In addition, an effect of preventing or treating inflammation or immunological diseases by the isolated and synthesized Ramalin (Korea Patent No. 10-1290745) and an effect of preventing or treating liver fibrosis and liver cirrhosis by the isolated and synthesized Ramalin (Korea Patent No. 10-1326256) have been found. However, an effect of preventing or treating neurodegenerative diseases by Ramalin has been not yet known.

Accordingly, the present inventors made all efforts to develop effective strategies for the treatment of AD and AD-like diseases, and as a result, confirmed that Ramalin inhibited BACE1 expression and expression of an inflammatory marker such as an NLRP inflammasome protein to inhibit production of amyloid and significantly improve a cognitive function in a AD model mouse and completed the present disclosure.

SUMMARY OF INVENTION

An object of the present disclosure provides a pharmaceutical composition for treating or preventing neurodegenerative diseases, comprising Ramalin as an active ingredient.

Another object of the present disclosure provides a food composition for preventing or treating neurodegenerative diseases, comprising Ramalin as an active ingredient.

DETAILED DESCRIPTION OF THE INVENTION

According to an aspect of the present disclosure, there is provided a pharmaceutical composition for treating or preventing neurodegenerative diseases, comprising Ramalin represented by the following Chemical Formula I as an active ingredient.

[Chemical Formula I]

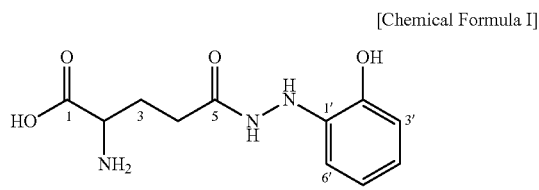 [SMILES: NC(CCC(=O)NNc1ccccc1O)C(=O)O]

According to another aspect of the present disclosure, there is provided a food composition for treating or preventing neurodegenerative diseases, comprising Ramalin represented by the Chemical Formula I as an active ingredient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A illustrates that experimental groups administered with Ramalin for 4 weeks find a platform under the water surface faster than a control group (vehicle); FIG. 2B illustrates that as a result of a probe test performed on the 6th day after a water maze test starts, Ramalin has an effect of improving a memory retention ability of a dementia animal model; FIG. 2C illustrates that there is no difference between experimental groups by measuring a swimming speed of experimental animal groups; and FIG. 2D illustrates that in order to evaluate a spatial memory ability, a Y-maze test is performed, and as a result, in an experimental group administered with Ramalin (20 mg/kg) for 4 weeks, a spontaneous alternation behavior is largely increased.

FIG. 3A illustrates that it is observed by a micrograph that an Aβ staining degree in the cortex and the hippocampus is reduced in an animal administered with Ramalin; FIG. 3B and FIG. 3C illustrate that it is confirmed by an image analysis quantification that the number of Aβ senile plaques is also reduced by administration of Ramalin in both the cortex and the hippocampus; and FIG. 3D and FIG. 3E illustrate that it is confirmed that as a result of measuring water-soluble Aβ using ELISA, both Aβ40 and Aβ42 are decreased in a Ramalin-administered group.

FIG. 4A illustrates that it is confirmed that the expression of BACE1 is decreased by Ramalin administration through an immunochemical staining method using a specific antibody to BACE1 which is an enzyme producing Aβ in the animal's cortex after administration of Ramalin; FIG. 4B illustrates that it is confirmed that the expression of BACE1 is decreased by Ramalin administration through an immunochemical staining method using a specific antibody to BACE1 which is an enzyme producing Aβ in the animal's hippocampus after administration of Ramalin; FIG. 4C illustrates that it is confirmed that BACE1 and C99 which is a Aβ precursor and a substrate of BACE1 is also decreased in the brain tissue of a Ramalin-administered animal when an level of protein is measured by a western blotting method; FIG. 4D illustrates the statistical value of the level of protein measured by the western blotting method; and FIG. 4E illustrates that it is confirmed that expression of a transcriptome (mRNA) of BACE1 in the brain tissue of an animal with dementia is decreased by Ramalin administration.

FIG. 5A illustrates that it is confirmed that protein levels of iNOS and COX-2 in the brain tissue of an animal with dementia are decreased by administration of Ramalin; and FIG. 5B and FIG. 5C illustrate the statistical values of the levels of proteins measured by a western blotting method.

FIG. 6A illustrates that levels of phosphorylated stress kinases p38, JNK and ERK in the brain tissue of an animal with dementia are decreased by administration of Ramalin; and FIG. 6B illustrates the statistical values of the levels of proteins p38, JNK and ERK measured by a western blotting method.

FIG. 7A illustrates that the levels of inflammasome constituent proteins NALP1, NALP3, caspase-1, IL-1β, TLR4, and XIAP in the brain tissues of animals with dementia are largely decreased by administration of Ramalin; and FIG. 7B illustrates the statistical values of the levels of the proteins NALP1, NALP3, caspase-1, IL-1β, TLR4, and XIAP measured by a western blotting method.

FIG. 8A illustrates that it is confirmed that when an inflammatory response is induced by treating LPS in the microneuroglial cells, largely increased NO is completely inhibited by treatment of Ramalin; FIG. 8B illustrates that it is confirmed that expression of main factors iNOS and COX-2 of inflammatory signaling increased by LPS in the microneuroglial cells is completely inhibited by Ramalin through a western blotting; FIG. 8C illustrates the statistical values of the level of iNOS measured by a western blotting method; and FIG. 8D illustrates the statistical values of the level of COX-2 measured by a western blotting method.

FIG. 9A illustrates that it is confirmed that NF-κB (phosphorylated p65) inhibited by LPS in the microneuroglial cells is decreased by treatment of Ramalin; FIG. 9B illustrates the statistical values of NF-κB (phosphorylated p65) inhibited by LPS in the microneuroglial cells; FIG. 9C illustrates that it is confirmed that activated stress kinases p38, JNK, and ERK in the microneuroglial cells treated with LPS are inhibited by treatment of Ramalin; and FIG. 9D illustrates the statistical values of stress kinases inhibited by LPS in the microneuroglial cells.

FIG. 10A illustrates that it is confirmed that the expressions of inflammasome constituent molecules NALP1, NALP3, and Caspase-1 and BACE1, which is a production enzyme of TLR4 and Aβ as congenital immunoreceptors, increased by LPS in the microneuroglial cells are inhibited by treatment of Ramalin through a western blotting method; and FIG. 10B illustrates the statistical values of the levels of the inflammasome constituent molecules and the congenital immunoreceptors measured by a western blotting method.

BEST MODE FOR CARRYING OUT THE INVENTION

Figure 1:
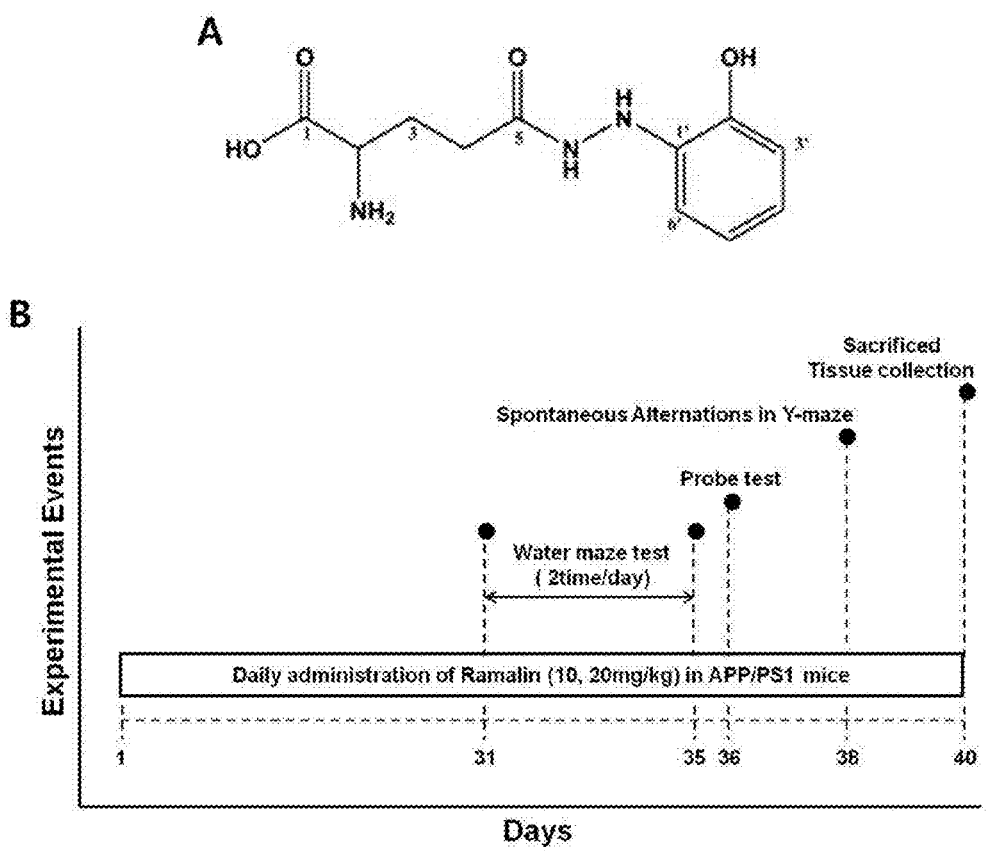
FIG. 1A is a schematic diagram of a chemical structure of Ramalin and FIG. 1B is a schematic diagram of an animal experimental plan for testing a behavioral function after the treatment of Ramalin.

Unless otherwise defined, all technical and scientific terms used in this specification have the same meaning as those commonly understood by those skilled in the art. In general, the nomenclature used in this specification is well-known and commonly used in the art.

In the present disclosure, a new learning and memory impairment prevention effect of γ-glutamyl-N'(2-hydroxyphenyl)hydrazide (Ramalin) which is a compound having a molecular formula of $C_{11}H_{16}N_3O_4$ isolated from Ramalina terebrata which is a lichen in Antarctica is identified.

Therefore, an aspect of the present disclosure relates to a pharmaceutical composition for treating or preventing neurodegenerative diseases, comprising Ramalin represented by the following Chemical Formula I as an active ingredient.

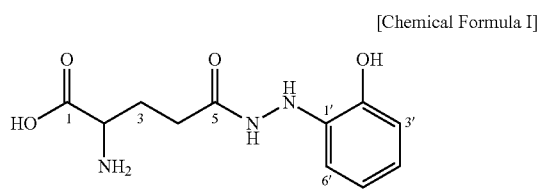 [SMILES: NC(CCC(=O)NNc1ccccc1O)C(=O)O]

[Chemical Formula I]

In the present disclosure, the neurodegenerative disease may be selected from a group consisting of Alzheimer's disease, Parkinson's disease, Lou Gehrig's disease, Pick's disease, Creutzfeldt-Jakob disease, Huntington's disease and dementia, and preferably Alzheimer's disease, but is not limited thereto.

In the present disclosure, the Ramalin may inhibit expression of BACE1 and expression of a NALP inflammasome protein. Further, the Ramalin may inhibit expression of signaling pathway proteins of inflammatory mediators of iNOS, COX-2, and MAPK.

The composition comprising Ramalin of the present disclosure may further include pharmaceutical acceptable and suitable carriers, excipients or diluents according to a general method. The carrier, the excipient, and the diluent which may be included in the composition comprising the compound may be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil.

The composition comprising Ramalin of the present disclosure may have any one formulation selected from a group consisting of a powder, a pill, a granule, a capsule, a suspension, a solution, an emulsion, a syrup, a sterilized aqueous solution, a nonaqueous solution, a suspension, a lyophilizing agent, and a suppository.

When the composition is formulated, the formulation may be prepared by using a diluent or an excipient, such as a filler, an extender, a binder, a wetting agent, a disintegrating agent, and a surfactant, which are generally used. A solid formulation for oral administration includes a tablet, a pill, a powder, a granule, a capsule, and the like, and the solid formulation may be prepared by mixing the compound with at least one excipient, for example, starch, calcium carbonate, sucrose or lactose, gelatin, and the like. Further, lubricants such as magnesium stearate and talc may be used in addition to simple excipients. A liquid formulation for oral administration may correspond to a suspension, a solution, an emulsion, a syrup, and the like, and may include various excipients, for example, a wetting agent, a sweetener, an aromatic agent, a preserving agent, and the like in addition to water and liquid paraffin which are commonly used simple diluents. A formulation for parenteral administration includes a sterilized aqueous solution, a non-aqueous solution, a suspension, an emulsion, and a lyophilizing agent, and a suppository. As the non-aqueous solution and the suspension, propylene glycol, polyethylene glycol, vegetable oils such as olive oil, injectable ester such as ethyl oleate, and the like may be used. As a matter of the suppository, witepsol, macrogol, tween 60, cacao butter, laurin butter, glycerogelatin, and the like may be used.

A preferable dose of the compound of the present disclosure varies according to a state and a weight of a patient, the degree of the disease, a drug form, and administration route and period, but may be properly selected by those skilled in the art. However, for a preferable effect, the compound of the present disclosure may be administered with 0.001 to 100/kg, preferably 0.01 to 10/kg per day. The compound may be administered once a day and orally administered several times a day. The dose does not limit the scope of the present disclosure in any way.

Another aspect of the present disclosure relates to a food composition for treating or improving neurodegenerative diseases, comprising Ramalin represented by the following Chemical Formula I as an active ingredient.

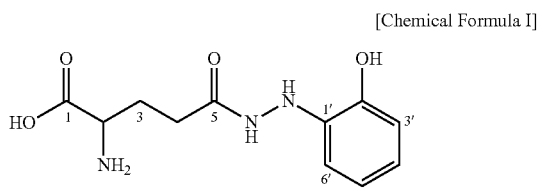 [SMILES: NC(CCC(=O)NNc1ccccc1O)C(=O)O]

[Chemical Formula I]

The food composition of the present disclosure includes all forms including functional food, nutritional supplement, health food, and food additives. The type of health functional food may be prepared into various forms according to a general method which is known in the art. For example, as the health food, the Ramalin of the present disclosure may be prepared and drunken in forms of teas, juices, and drinks, or taken by granulation, encapsulation, and powdering. Further, the functional food may be prepared by adding the Ramalin of the present disclosure to beverages (including alcoholic beverages), fruits and their processed foods (e.g., canned fruits, bottled foods, jam, marmalade, etc.), fish, meat and their processed food (e.g., ham, sausage, corn beef, etc.), breads and noodles (e.g., udon noodles, buckwheat noodles, ramen noodles, spaghetti, macaroni, etc.), juices, various drinks, cookies, taffy, dairy products (e.g., butter, cheese, etc.), edible vegetable oils, margarine, vegetable proteins, retort foods, frozen foods, various seasonings (e.g., soybean paste, soy sauce, sauce, etc.), and the like.

Further, the health functional food includes various forms, such as functional food, nutritional supplements, health food, and food additives, as the food composition, and may be provided in various forms according to a general method which is known in the art, for example, by preparing the aforementioned Ramalin in forms such as tea, juice, and drink or granulating, encapsulating, and powdering the Ramalin, or adding the compound or the extract to various foods including beverages, fruits and their processed foods, fish, meat and their processed foods, breads, noodles, seasonings, and the like.

EXAMPLES

Hereinafter, the present disclosure will be described in more detail through Examples. However, the present disclosure is not limited to the exemplary embodiments disclosed below, but can be implemented in various forms. The following exemplary embodiments are described in order to enable those of ordinary skill in the art to embody and practice the invention.

Example 1: Isolation/Synthesis of Ramalin and Animal Model Design

In the following Example of the present disclosure, Ramalin was isolated (Korea Patent No. 10-1025612) and used by the isolation method by using methanol from Ramalina terebrata collected in the Barton Peninsula (S62°13.1, W58°47.0) of the King George Island in January, 2008, or stable Ramalin having the same efficacy as Ramalin derived from natural products was synthesized (Korea Patent No. 10-1182334) and used (FIG. 1A).

While semi-conjugated transgenic mice APP/PS1 (APPswe/PSEN1dE9) of C57BL/6J species were kept in 12 hrs-light and 12 hrs-dark, an experiment was performed. 7-month-old female APP/PS1 mice were divided into three groups (control, 10 mg/kg Ramalin, and 20 mg/kg Ramalin) in which six mice were included in one group and the Ramalin was orally administered to the mice once a day for 38 days.

A Morris water maze test was performed from the 31-st day to the 35-th day, and a memory retention test on the 36-th day and a Y maze test on the 38-th day were performed. On the 40-th day, the mice were sacrificed and then the brain tissues were stored at −70° C. (FIG. 1B).

Example 2: Morris Water Maze Test

In order to confirm a memory improvement effect of Ramalin on APP/PS1 transgenic mice, a known conventional Morris method was slightly modified and performed. A water bath had a circular shape with a height of 35 cm and a diameter of 100 cm and was added with a nontoxic water-soluble black dye and maintained at a water temperature of 20° C. The water bath was divided into four sections and a black platform (with a height of 10 cm and a diameter of 8 cm) was positioned below about 1 cm from the surface in the middle of one of the four sections. Mice which started to swim in the platform of the water bath with various spatial clues were observed by a video system (Ethovirion system Noldus, Wageningen, Netherlands). A water maze education was given twice a day when the mice did not find the platform for 60 seconds. Each trial was performed after a break time of 15 minutes and performed continuously for 4 days. Times which were taken in each experiment by each mouse were measured to obtain an average value. When the mouse found that platform, the mouse stayed for 10 seconds, and when the mouse did not find the platform within 120 seconds, an experimenter induced the mouse to stay in the platform for 10 seconds. On the 6-th day, the platform was removed from the water bath and then a probe test was performed for 60 seconds.

Figure 2:
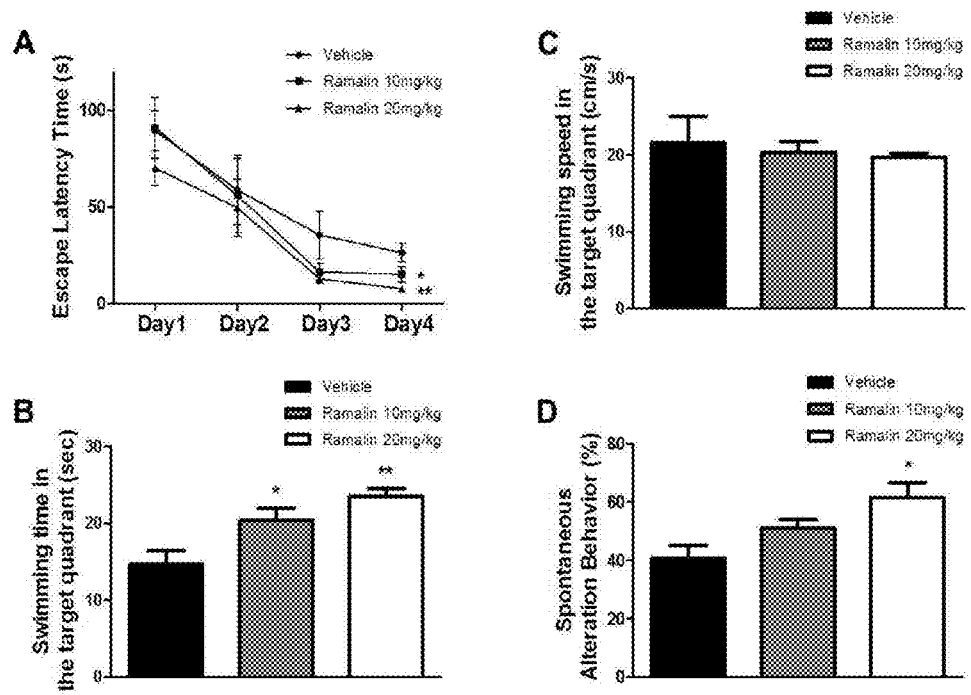
FIGS. 2A through 2D illustrate a result illustrating an effect of preventing learning and memory disorders according to the administration of Ramalin by targeting APP/PS1 transformed mice which are an animal model having Alzheimer's disease.

After improving a hippocampal function by administration of Ramalin to APP/PS1 transgenic mice for 4 weeks, a Morris water maze test was performed and Ramalin was also administered for 1 week during the test. As a result, it was confirmed that after a position of the platform was trained, a time to arrive at the platform was shortened by the improved memory. In a group administered with Ramalin (10 and 20 mg/kg), the time to arrive at the platform was shortened on the 4-th day (FIG. 2A). Further, after the platform was removed at the last day, when the time to stay in a target quadrant was measured, the time was increased depending on the concentration (10 and 20 mg/kg) of Ramalin (FIG. 2B). In the Ramalin-administered group and the control group, there was no difference in swimming speed (FIG. 2C).

Example 3: Y Maze Test

In a Y maze, three arms were extended in a Y shape, and each arm was positioned at an angle of 120° with a length of 40 cm, a height of 12 cm, and a width of 3 cm. The bottom and the wall of the maze were made of an opaque dark polyvinyl plastic material, and it was recorded that the mice were first positioned in sequence (i.e., ABCAB etc.) on one arm and then passed through the arm for 8 minutes. The movement of the mouse was represented by a cross number, and only when the mouse continuously passed through three arms, it was defined as once crossing (i.e., ABC, CAB, or BCA, but not BAB). The arms of the maze were cleaned by clearly removing the smell, and finally, the Ramalin was administered (10 and 20 mg/kg) and then memory damage inhibition by Ramalin after one hour was measured. A cross ratio is defined as follows.

% cross=[(cross number)/(total arm passage number)]×100

As a result, it was confirmed that in the group administered with Ramalin at a concentration of 20 mg/kg, the memory was improved (FIG. 2D).

Example 4: Aβ Production and Neuritic Plaque Formation in APP/PS1 Mouse's Brain In order to examine an effect of Ramalin on accumulation of amyloid in a APP/PS1 mouse's brain, formation of Aβ40, Aβ42, and Aβ plaques in the Ramalin-administered group and the control group was analyzed. The accumulation of the Aβ plaque by treatment of Ramalin was confirmed by immunostaining the brain.

Figure 3:
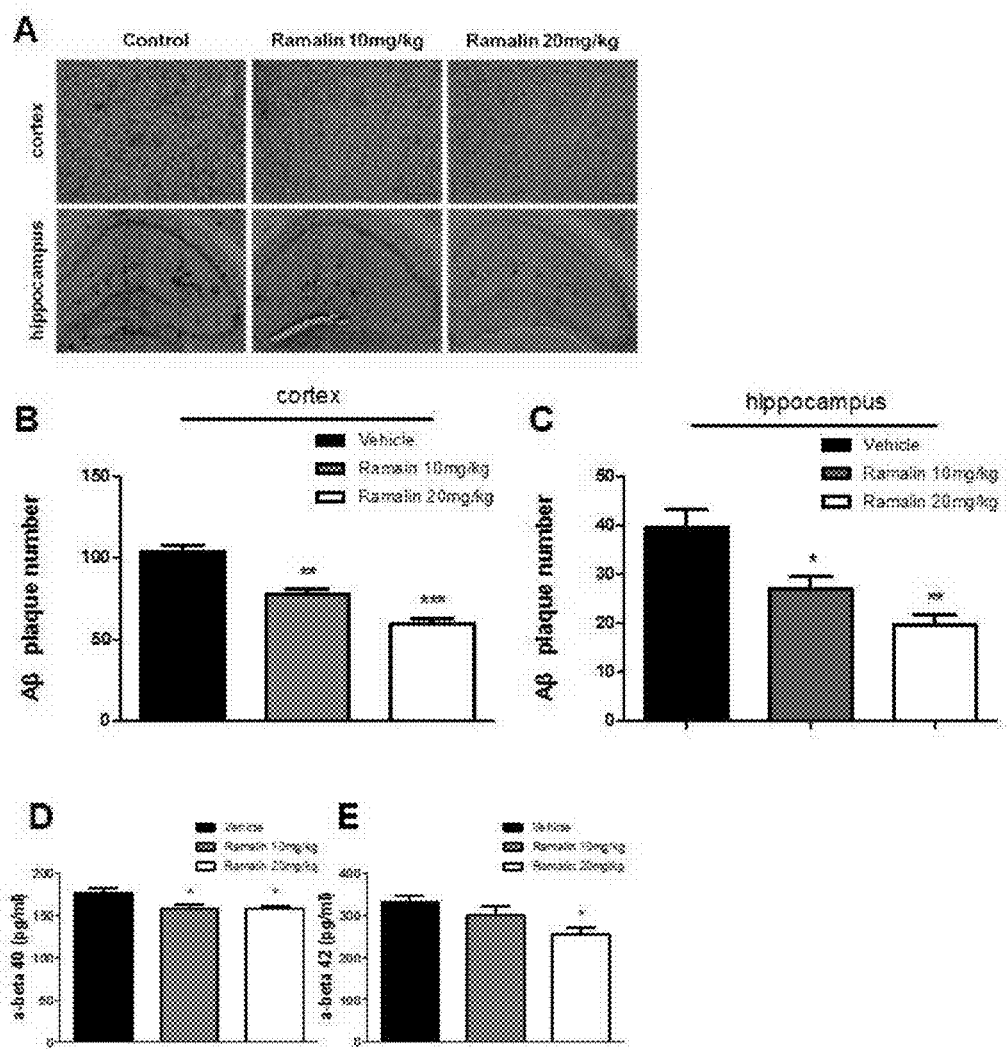
FIGS. 3A through 3E illustrate a result illustrating that formation of neuritic plaque and generation of Aβ are significantly reduced after administration of Ramalin in APP/PS1 transformed mice which are an animal model having Alzheimer's disease.

The brain tissue of the mouse was fixed with 4% paraformaldehyde, frozen with 30% sucrose at 4° C. for 48 hrs, and cut with a thickness of 45 μm. The plaque formation was confirmed by DAB staining using an anti-Aβ antibody (400:1, 4G8, Covance). As a result, in the brain cortex and the hippocampus of the Ramalin-administered group, the plaque formation was significantly reduced (FIG. 3B and FIG. 3C).

Further, the Aβ was quantified by a solid-phase sandwich ELISA system (IBL, 27713 and 27711). The brain tissue was homogenized with PBS containing 1× protease cocktail (Calbiochem), centrifuged at 4° C. and 13,000 rpm for 10 minutes, added with a standard Aβ of 100 μg and a sample per well, and O/N reacted with an Aβ antibody at 4° C., and then reacted with antimouse IgG-HRP at room temperature for 1 hr, washed, added with stabilized chromogen of 100 ul per well, dark-reacted at room temperature for 30 minutes, and then added with a stop solution, and analyzed at 450 nm. As a result, it was confirmed that in the APP/PS1 mouse's brain tissue, Aβ40, Aβ42, and the like were significantly reduced by treatment of Ramalin (FIG. 3D and FIG. 3E).

Example 5: Reduction of BACE1 Expression in Ramalin-Treated APP/PS1 Mouse's Brain In order to examine an effect of Ramalin on BACE1 expression in a APP/PS1 mouse's brain, BACE1 levels in the Ramalin-administered group and the control group were analyzed by immunofluorescent staining and western blotting. Further, BACE1 mRNA levels were analyzed by real-time polymerase chain reaction.

The immunofluorescent staining method was the same as the method in Example 4 and analyzed by using a BACE1 antibody (400:1, R&D system).

In order to perform the western blotting, in the APP/PS1 mouse's brain tissue, proteins were extracted by using a T-per (pierce) extraction buffer and complete mini protease inhibitor tablets (Roche). The extracted proteins were electrophoresed on 8-17% SDS-PAGE, transferred to 0.45 μM PVDF, and then confirmed with a BACE1 antibody (cell signaling).

The real-time polymerase chain reaction was performed by extracting total RNA with a ribospin RNA purification system (GeanAll) and RT was performed with RNA of 1 μg by using an iScript system cDNA synthesis kit (Bio-Rad). The real-time polymerase chain reaction was performed by using a CFX96™ system (Bio-Rad) and PCR amplification used SYBR Premix EX Taq™ II (TaKaRa Bio Inc.) and relative quantification was performed by a 2-ΔΔct method. Primers for respective genes are as follows.

```
                                       (SEQ ID NO: 1)
    BACE1:  forward 5'-ATGTGGAGATGACCGTAGGC-3'

(SEQ ID NO: 2)
    reverse 5'-TACACACCCTTTCGGAGGTC-3'

(SEQ ID NO: 3)
    GAPDH:  forward 5'-GACATCAAGAAGGTGGTGAA-3'

(SEQ ID NO: 4)
    reverse 5'-TGTCATACCAGGAAATAGGC-3'
```

BACE1 expression levels were represented by % for GAPDH expression levels.

Figure 4:
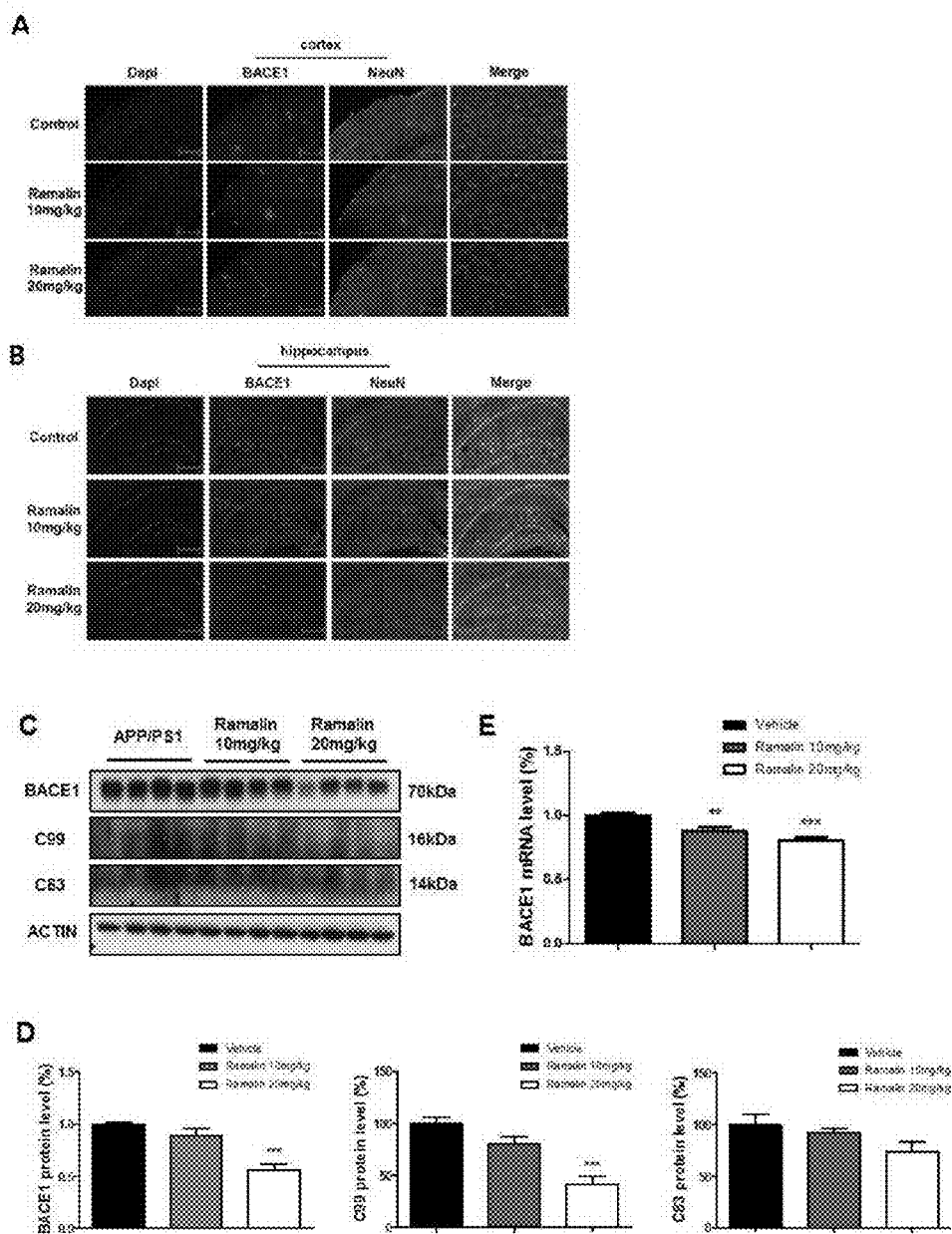
FIGS. 4A through 4E illustrate a result illustrating that as a result of confirming the inhibition of a BACE1 level in an APP/PS1 transformed mouse, which is an Alzheimer's disease animal model after administration of Ramalin, Ramalin has an effect of reducing levels of transcriptome and protein of BACE1 in the brain, and as a result, production of Aβ as a causative agent of dementia is reduced.

As a result, it was confirmed that a BACE1 immune response was decreased in the brain cortex and the hippocampus in the Ramalin-administered group by immunofluorescent staining (FIG. 4A). Next, in the Ramalin-treated APP/PS1 mouse's brain, protein expression of BACE1, C99 and C83 was measured. As a result, it was confirmed that the BACE1 expression was significantly decreased in a treatment condition of Ramalin for 1 month (FIG. 4D). Further, it was confirmed that an mRNA level of BACE1 was decreased with the treatment of Ramalin by the real-time polymerase chain reaction analysis (FIG. 4E).

Example 6: Effect of Treatment of Ramalin on iNOS, COX-2, MAPK and Inflammasome in APP/PS1 Mouse's Brain Ramalin was a well-known anti-inflammatory compound to inhibit production of nitric oxide and increase neuroprotection. Accordingly, an anti-inflammatory effect of Ramalin and an effect of Ramalin on neuronal inflammation in an APP/PS1 mouse, AD model were confirmed by production of nitric oxide.

Figure 5:
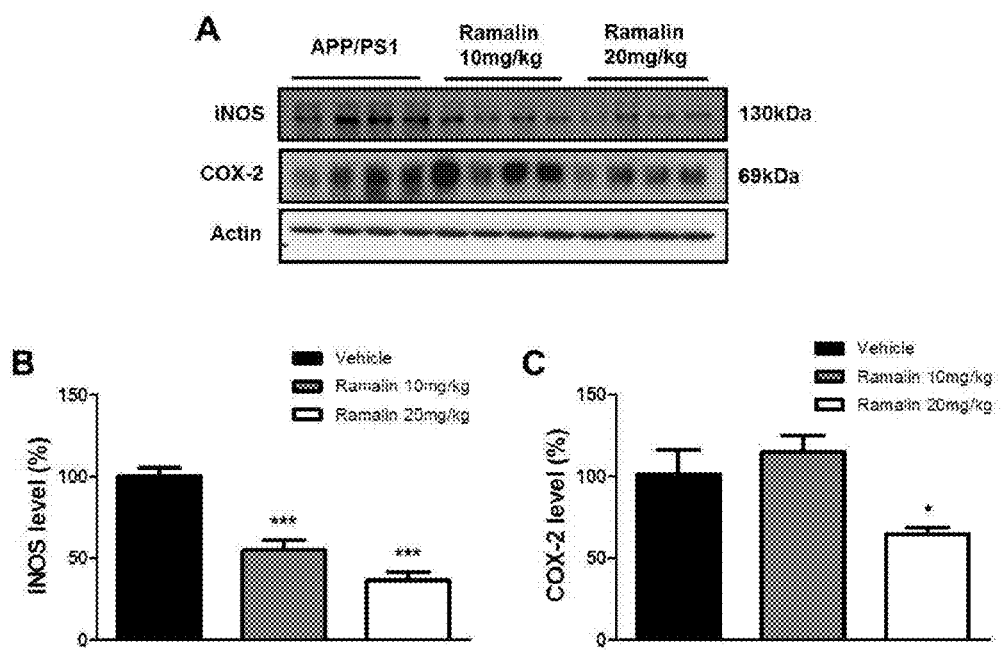
FIGS. 5A through 5C illustrate a result of confirming an effect of inhibiting expression of iNOS and COX-2 in an APP/PS1 transformed mouse's brain which is an Alzheimer's disease animal model after administration of Ramalin
Figure 6:
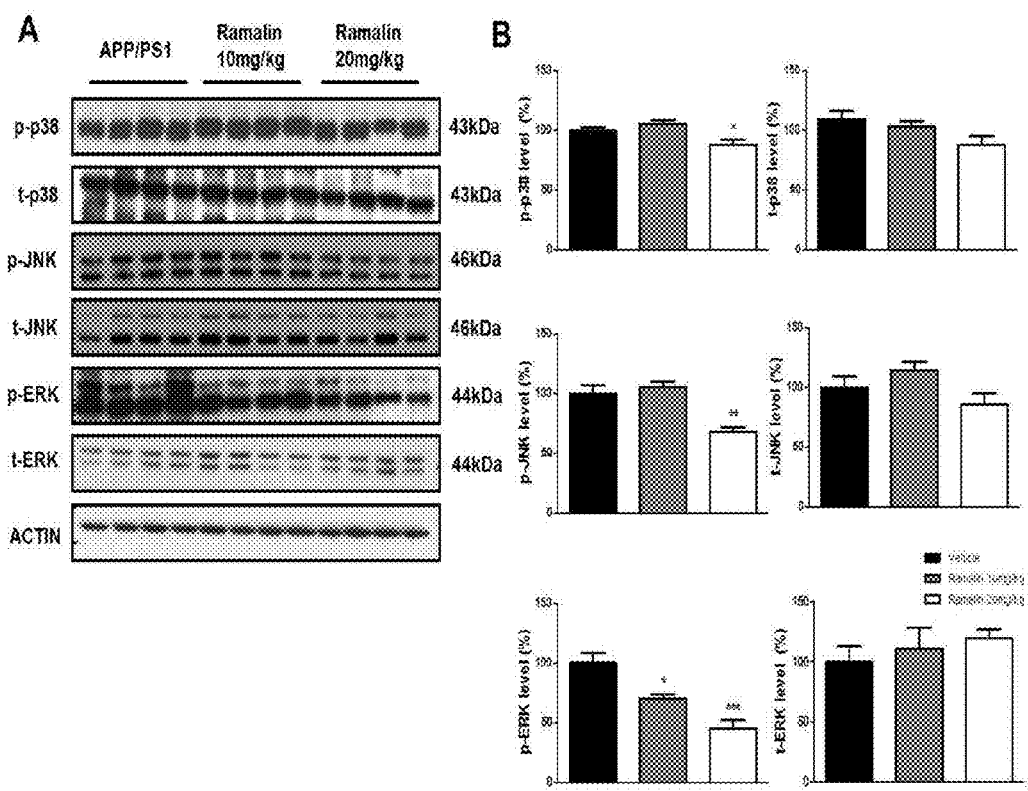
FIGS. 6A and 6B illustrate a result of confirming an effect on a MAPK signaling pathway protein in an APP/PS1 transformed mouse's brain which is an Alzheimer's disease animal model after administration of Ramalin.
Figure 7:
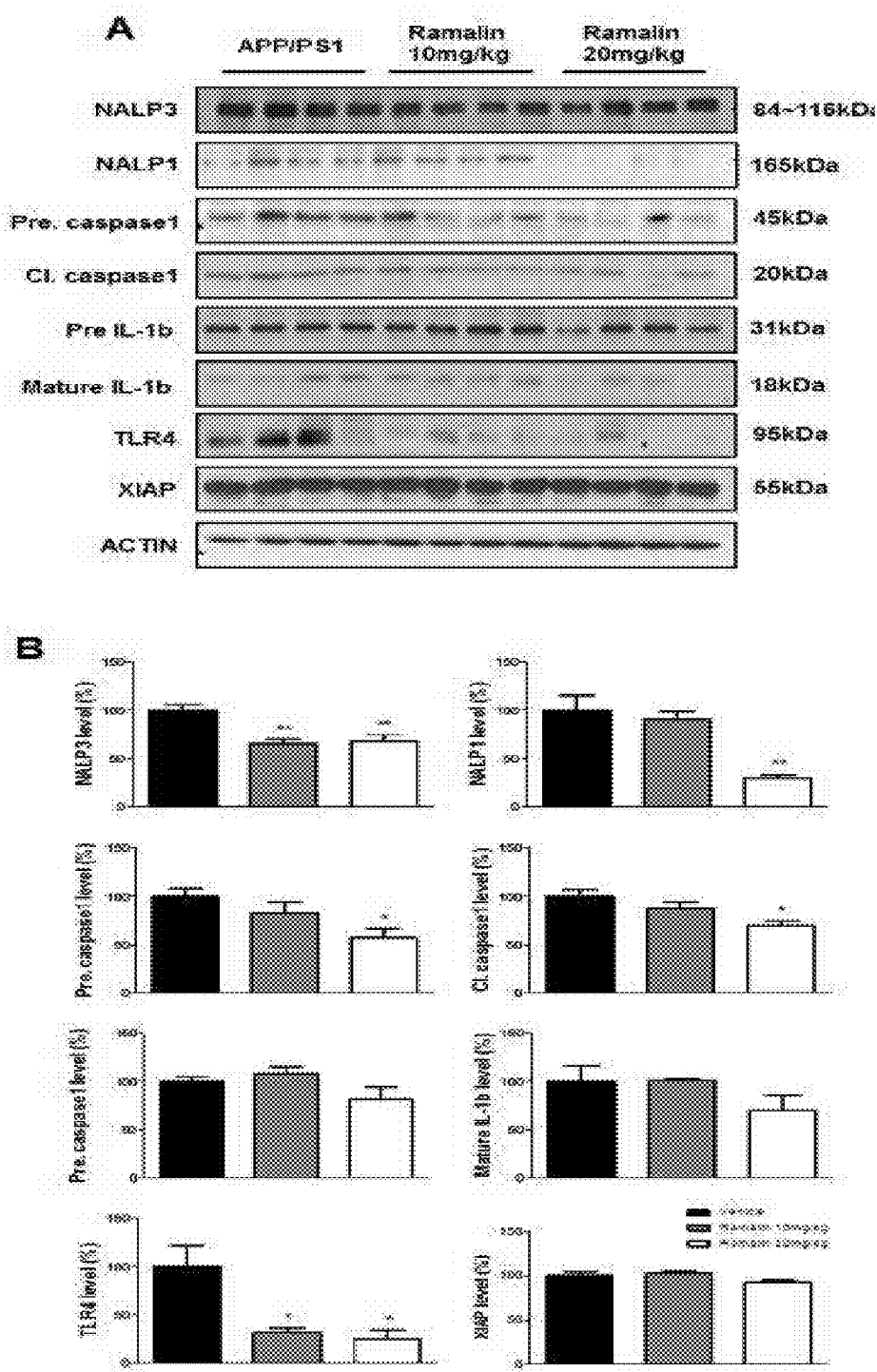
FIGS. 7A and 7B illustrate a result of confirming an effect on an inflammasome protein in an APP/PS1 transformed mouse's brain which is an Alzheimer's disease animal model after administration of Ramalin

As a result, it could be confirmed that expression of iNOS and COX-2 in the APP/PS1 mouse's brain was significantly inhibited by treatment of Ramalin (FIGS. 5A through 5C).

Further, an effect on expression of mitogen-activated protein kinases (MAPK) and NALP inflammasome proteins by treatment of Ramalin was analyzed. Protein expression of p38, JNK, ERK, NALP3, NALP1, Caspase1 and XIAP was confirmed by western blotting.

As a result, expression of p-p38, p-JNK, P-ERK, NALP1, NALP3, pre-caspase1, cleaved-caspase1, and TLR4 was decreased by treatment of Ramalin, but t-p38, t-JNK, t-ERK, pre-IL-1β and XIAP had no large difference (FIGS. 6A, 6B, 7A, and 7B).

Example 7: Effect of Ramalin on NO, iNOS and COX-2 Induced by LPS

HT-22 hippocampal cells and BV-2 microneuroglial cells were incubated in a $CO_2$ incubator at 37° C. with a DMEM (Hyclone, USA) containing 10% FBS and 1% pen/strep (Gibco, USA). Ramalin was dissolved in distilled water at a concentration of 0.1% (v/v) and used and cells in all experiments were incubated in a serum-free DMEM medium with or without LPS (1 μg/ml) by Ramalin at each concentration.

NO measurement was performed by Griess reaction with the culture medium and the BV-2 microneuroglial cells ($2.5 \times 10^5$ cell/well in 24 well plate) were pre-treated with Ramalin and then treated with LPS (1 μg/ml) for 24 hrs, and then the culture solution was analyzed. 50 μl of the culture solution of each sample was mixed with an equal level of Griess reagent [0.1% N-(1-naphthyl)-ethylenediamine dihydrochloride and 5% phosphoric acid containing 1% sulfanilamide] and dark-reacted for 10 minutes in a 96 well plate. The nitrate concentration was analyzed by a standard solution of sodium nitrate of the culture solution and measured at 540 nm.

Figure 8:
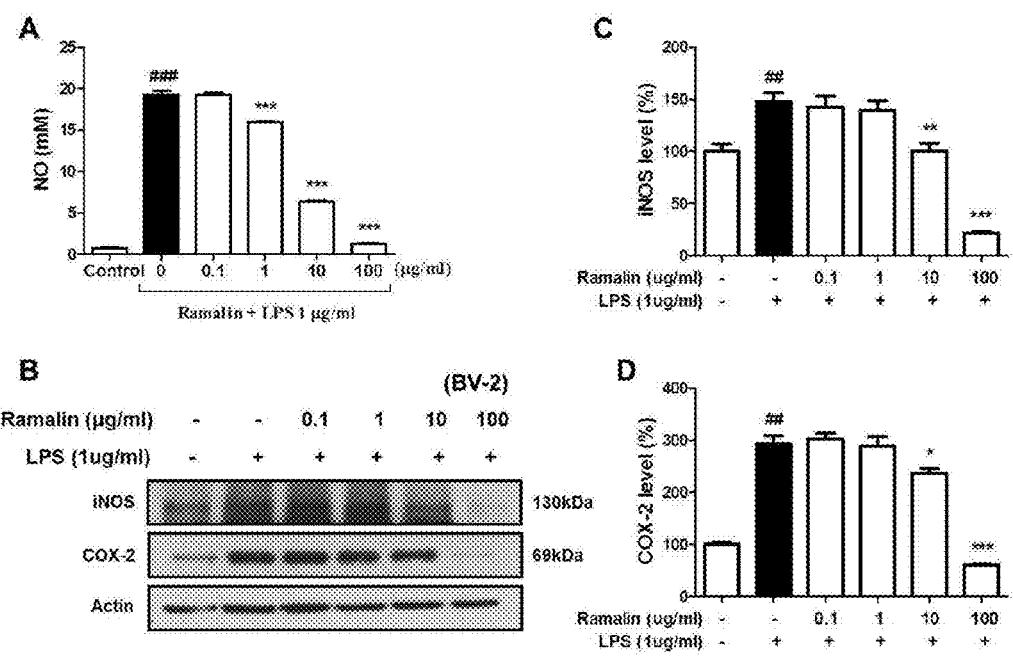
FIGS. 8A through 8D illustrate a result of confirming an effect of Ramalin on inflammation induced by LPS in the microneuroglial cells.
Figure 9:
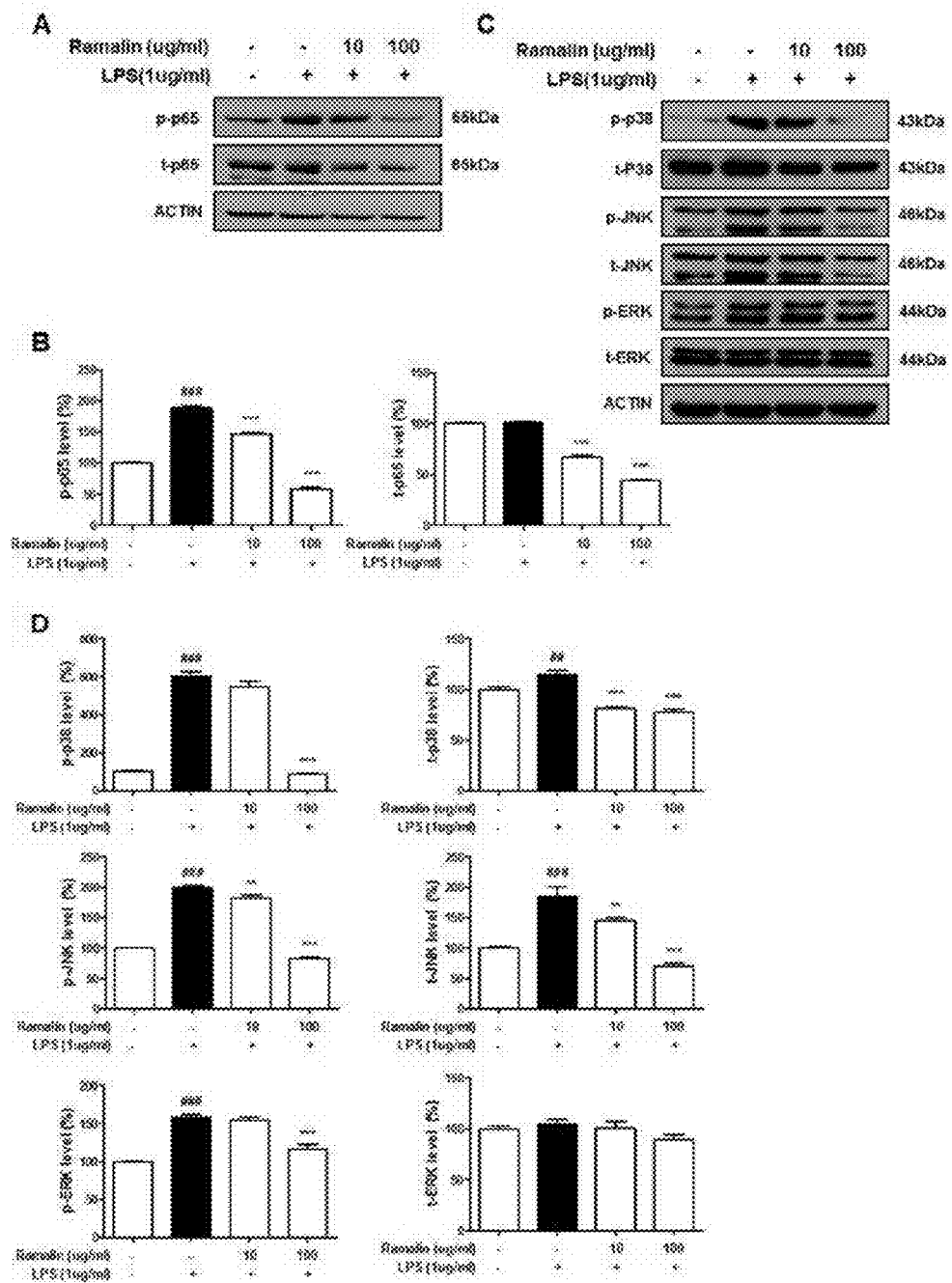
FIGS. 9A through 9D illustrate a result of confirming an effect of Ramalin on activities of NF-κB and MAPK induced by LPS in the microneuroglial cells.

As a result, in the BV-2 microneuroglial cells, NO production by 1 μg/ml LPS treatment was 18.52 μM and NO production was decreased to 15.17 μM by 1 μg/ml treatment of Ramalin and 5.64 μM by 10 μg/ml treatment of Ramalin. Further, the NO production was significantly inhibited as 0.53 μM by 100 μg/ml treatment of Ramalin (FIG. 8A).

After 1 μg/ml LPS treatment, iNOS and COX-2 protein levels analyzed by western blotting were increased at about 48% as compared with a control group, but the increased of 46.67% and 55.33% was inhibited again by 10 µg/ml treatment of Ramalin. Further, a significant increase of 126.3% and 232% of the iNOS and COX-2 protein levels was inhibited by 100 µg/ml treatment of Ramalin (FIGS. 8C and 8D).

Example 8: Effect of Ramalin on Phosphorylation of p38, JNK, ERK and NF-κB Induced by LPS and Inflammasome Protein As illustrated in FIGS. 8A through 8D, in the BV-2 microneuroglial cells, p38, JNK, ERK MAPK and NF-κB p65 are rapidly phosphorylated at ratios of 503.7%, 99%, 58% and 89% by 1 µg/ml LPS treatment as compared with a control group. However, phosphorylation of NF-κB is decreased to 41.67% and 131% by treatment of Ramalin of 10 and 100 µg/ml, and phosphorylation of p38, JNK and ERK MAPK is decreased by 516.5%, 116% and 42%. In addition, in the LPS-treated microneuroglial cells, the increased NF-κB (the phosphorylated p65) is decreased by Ramalin, and in the LPS-treated microneuroglial cells, activated stress kinases p38, JNK, and ERK are inhibited by treatment of Ramalin (FIGS. 9A through 9D).

Figure 10:
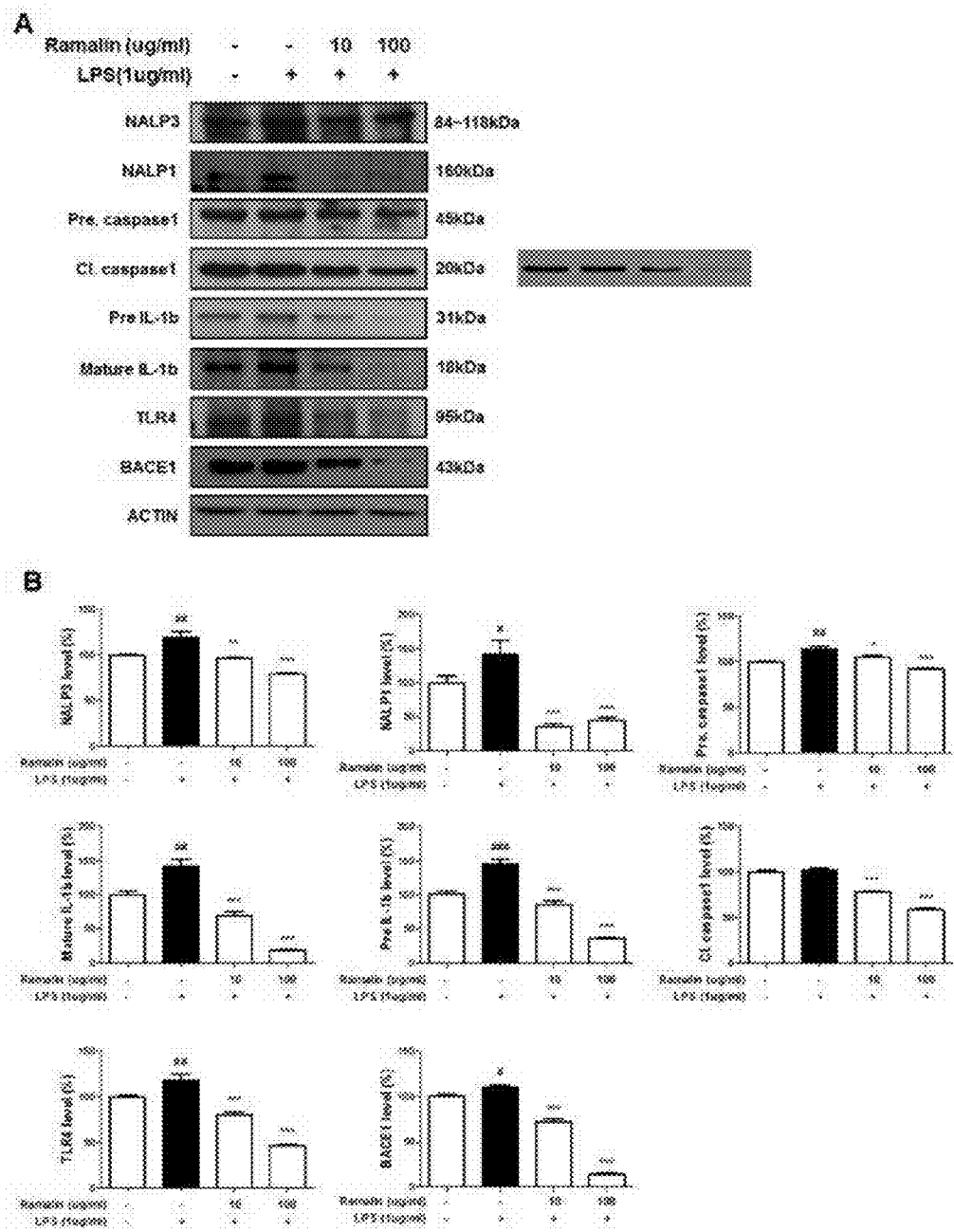
FIGS. 10A and 10B illustrate a result of confirming an effect of Ramalin on expressions of inflammasome, IL-1β, TLR4, and BACE1 induced by LPS in microneuroglial cells.

Further, in the BV-2 microneuroglial cells, it is shown that expression of inflammasome constituent molecules NALP1, NALP3, and Caspase-1 and BACE1 which is a production enzyme of TLR4 and Aβ as congenital immunoreceptors increased by LPS are significantly inhibited by treatment of Ramalin (FIGS. 10A and 10B).

Ramalin according to the present disclosure has an effect of improving a cognitive ability by inhibiting the expression of an inflammatory factor containing an NLRP inflammasome protein and BACE1, and is thus useful for preventing or treating memory disorder and neurodegenerative diseases.

Although the specific part of the present disclosure has been described in detail, it is obvious to those skilled in the art that such a specific description is just a preferred embodiment and the scope of the present disclosure is not limited. Thus, the substantial scope of the present disclosure will be defined by the appended claims and equivalents thereof.

What is claimed is:

1. A method of treating Alzheimer's disease, comprising administering a pharmaceutical composition comprising Ramalin represented by a following Chemical Formula I as an active ingredient:

[Chemical Formula I]

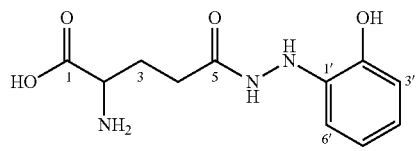

2. The method of claim 1, wherein the Ramalin inhibits expression of beta secretase 1 (BACE1) and expression of an inflammasome protein including the following domains: (i) neuronal apoptosis inhibitor protein domain, (ii) class 2 transcription activator of major histocompatibility complex domain, (iii) heterokaryon incompatibility domain, (iv) telomerase-associated protein 1 domain, (v) leucine-rich repeat domain, and (vi) pyrin domain.

3. The method of claim 1, further comprising pharmaceutical acceptable carriers, excipients or diluents.

4. A method of improving Alzheimer's disease, comprising administering food composition comprising Ramalin represented by a following Chemical Formula I as an active ingredient:

[Chemical Formula I]

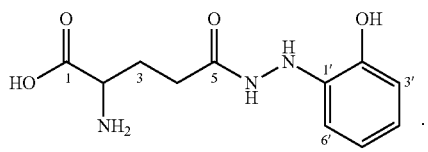

* * * * *

UNITED STATES PATENT AND TRADEMARK OFFICE
CERTIFICATE OF CORRECTION

PATENT NO. : 9,968,576 B2
APPLICATION NO. : 15/520100
DATED : May 15, 2018
INVENTOR(S) : Joung Han Yim Page 1 of 1

It is certified that error appears in the above-identified patent and that said Letters Patent is hereby corrected as shown below:

On the Title Page

Under the heading "Foreign Patent Documents" the fourth line "JP 20103-534517 A 9/2013" should be deleted.

Signed and Sealed this
Twenty-sixth Day of June, 2018

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: BACE1-f

<400> SEQUENCE: 1
atgtggagat gaccgtaggc                                                 20

<210> SEQ ID NO 2
<211> LENGTH: 20
<212> TYPE: DNA
<213> ORGANISM: Artificial Sequence
<220> FEATURE:
<223> OTHER INFORMATION: BACE1-r

<400> SEQUENCE: 2
tacacaccct ttcggaggtc                                                 20

<210> SEQ ID NO 3
<211> LENGTH: 20
<212> TYPE: DNA
<213> ORGANISM: Artificial Sequence
<220> FEATURE:
<223> OTHER INFORMATION: GAPDH-f

<400> SEQUENCE: 3
gacatcaaga aggtggtgaa                                                 20

<210> SEQ ID NO 4
<211> LENGTH: 20
<212> TYPE: DNA
<213> ORGANISM: Artificial Sequence
<220> FEATURE:
<223> OTHER INFORMATION: GAPDH-r

<400> SEQUENCE: 4
tgtcatacca ggaaataggc                                                 20
```